United States Patent [19]
Fremstad

[11] Patent Number: 5,472,436
[45] Date of Patent: Dec. 5, 1995

[54] OCULAR APPLIANCE FOR DELIVERING MEDICATION

[76] Inventor: Daria A. Fremstad, 80 Forrest Lake Cir. Rd., Pendergrass, Ga. 30567

[21] Appl. No.: 280,843

[22] Filed: Jul. 26, 1994

[51] Int. Cl.[6] .................................................. A61M 35/00
[52] U.S. Cl. ..................... 604/294; 604/890.1; 424/427; 623/4
[58] Field of Search .................................. 604/294, 297, 604/890.1, 891.1; 424/427, 428; 623/4; 606/166

[56] References Cited

U.S. PATENT DOCUMENTS

| | | | |
|---|---|---|---|
| 3,416,530 | 7/1968 | Ness | 424/427 |
| 3,630,200 | 12/1971 | Higuchi . | |
| 3,995,635 | 12/1976 | Higuchi et al. | 604/294 |
| 4,179,497 | 12/1979 | Cohen et al. | 604/294 |
| 4,343,787 | 8/1982 | Katz | 604/294 |
| 4,484,922 | 11/1984 | Rosenwald | 604/893 |
| 5,354,331 | 10/1994 | Schachar | 623/4 |

Primary Examiner—Randall L. Green
Assistant Examiner—Mark O. Polutta
Attorney, Agent, or Firm—Michael A. Mann

[57] ABSTRACT

A device for delivering an anesthetic to the eye, comprising a thin, porous, substantially planar annular body. The inner diameter of the device is slightly greater than the diameter of the limbus or corneal-scleral junction of the eye, and the outer diameter, slightly smaller than the arcuate distance between the upper and lower conjunctival sacs. The device is made of a flexible material such as methylcellulose-based filter paper, thus, it is able to flex to conform to the shape of the eyeball. The device is positioned in the eye with the inner edge circumscribing the limbus and the outer edge extending into the conjunctival sacs. A liquid such as a topical anesthetic, antibiotic, and so forth is added to the body by means of an eye dropper or other suitable means. The liquid spreads rapidly and uniformly throughout the body and diffuses into the eye. If desired, a plurality of equally-spaced radial slits may be formed in the body to enable it to conform to the shape of the eye.

17 Claims, 1 Drawing Sheet

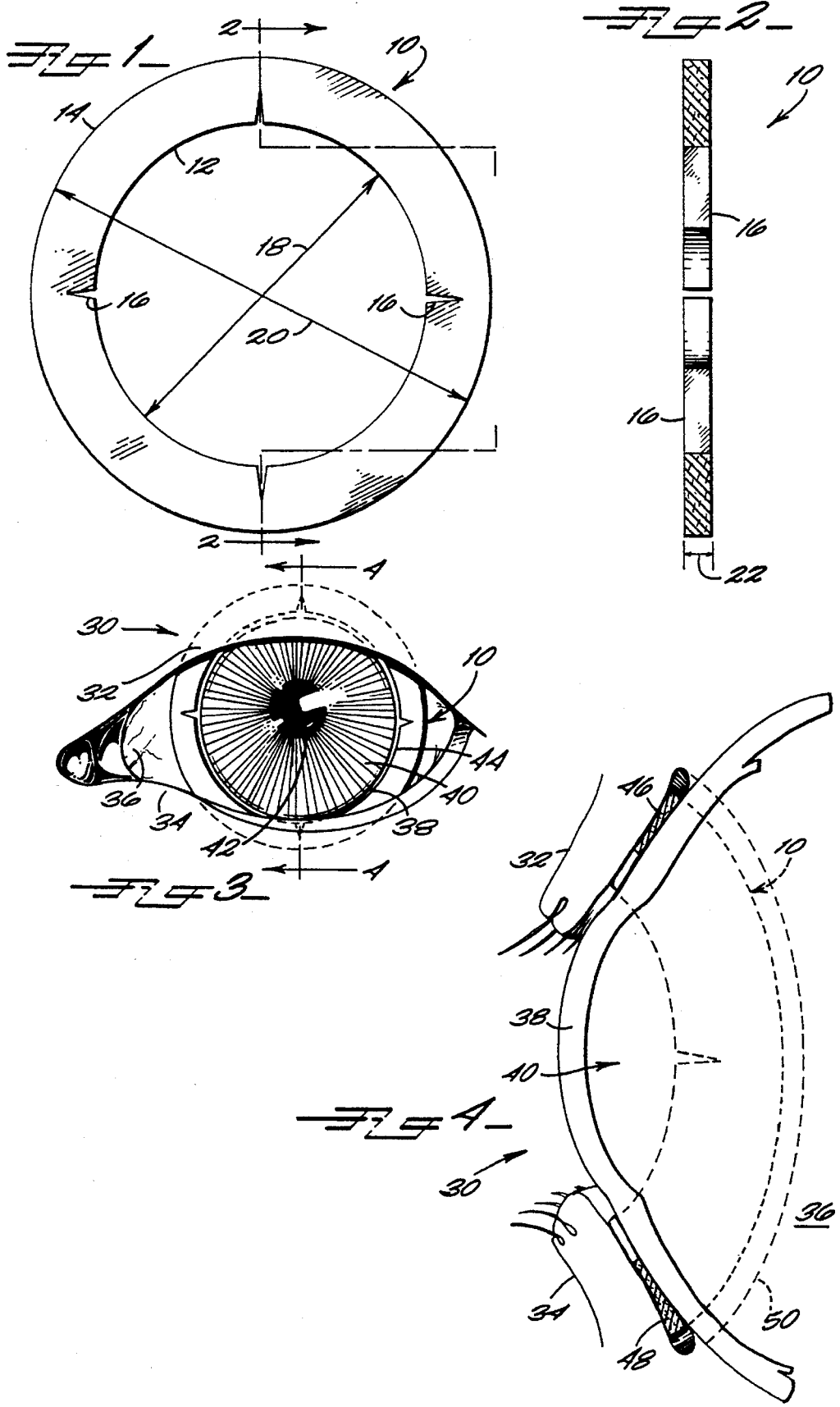

OCULAR APPLIANCE FOR DELIVERING MEDICATION

BACKGROUND OF THE INVENTION

1. Field of the Invention

The present invention relates to a device for delivering medicative liquids to the eye. In particular, the present invention relates to a porous, flexible ocular appliance for delivering short-duration topical anesthetic agents and other medication to the eye.

2. Discussion of Background

Topical anesthetics, antibiotics and other medications are usually delivered to the eye by placing liquids or salves directly into the eye with a squeeze tube, eye dropper, or as an eye wash. The person administering the medication may place a finger over the tear duct to help keep the medication in the eye and prevent it from entering the patient's system and being carried throughout the body. Once placed in the eye, the liquid is dispersed over the eyeball by the lacrimal fluids (tears).

Liquids can also be delivered using contact lenses and other types of ocular inserts or appliances. So-called "soft" contact lenses made of highly porous plastic can absorb half or more of their volume in water or other fluids. This type of lens can be soaked in a liquid medication and then inserted into the eye to deliver the medication. Other types of ocular inserts designed for long-term dispensing of medication include a frustospherical, annular ring made of a semipermeable polymeric material, shaped to conform to the curvature of the eye (Rosenwald, U.S. Pat. No. 4,484,922). The device is placed on the cornea, and extends over the eyeball and into the conjunctival sacs behind the upper and lower eyelids. Hughes, et al. (U.S. Pat. No. 4,201,210) and Higuchi, et al. (U.S. Pat. No. 3,995,635) describe flexible tubular devices sized for insertion into the conjunctival sac of the eye. Both devices can be made of bioerodable materials, or inert tubing with holes for distributing the medication.

The corneal region of the eye is highly sensitive to the presence of foreign bodies, which can be a source of discomfort, irritation and even injury to the patient. The sensation of a foreign body in the eye—including an insert designed for the delivery of medication—stimulates natural defense mechanisms which protect the eye against injury. For example, the lacrimal glands become more active, producing tears that dilute liquids and wash solid objects from the eye; the eyeball tends to rotate up and down while the eyelids blink in order to expel the object. When liquid medication is administered with an eye dropper or the like, the liquid may not be distributed uniformly over the eyeball, and a significant portion may spill out of the eye. This is a particular problem in the case of topical anesthetic agents used for ophthalmic surgery, since it is important to provide the correct dose of the selected anesthetic and also to distribute it uniformly over the eye.

Many types of ocular inserts are designed for long-term delivery of medication, and thus, are not suited for the relatively rapid (no more than a few minutes) delivery time needed for topical anesthetics. Furthermore, many inserts are bulky and uncomfortable, or must be shaped to fit the eye. Consequently, there is a need for an insert designed for the rapid delivery of liquid medication to the eye. The insert should be capable of delivering the medication uniformly, be comfortable for the patient, easy to use, usable on all or most patients without the need for individual fitting, and simple and economical to manufacture.

SUMMARY OF THE INVENTION

According to its major aspects and broadly stated, the present invention is a device for delivering a liquid medication to the eye. The device comprises a thin, porous, substantially planar annular body, with an inner diameter slightly greater than the diameter of the limbus of the eye, and an outer diameter slightly smaller than the arcuate distance between the upper and lower conjunctival sacs. The device is made of a flexible material such as methylcellulose-based filter paper, thus, it can conform to the shape of the eyeball.

The device is positioned in the eye with the inner edge circumscribing the limbus and the outer edges extending into the conjunctival sacs. A small amount of lacrimal fluid may be absorbed by the device, helping it flex and conform to the shape of the eyeball. A liquid medication (topical anesthetic, antibiotic, etc.) is added to the body by means of an eye dropper or other suitable means. The liquid spreads by wicking rapidly throughout the device and is diffused into the eye.

The dimensions of the present invention constitute an important feature thereof. The device has a generally annular shape, sized to allow placement on the eye with the inner edge circumscribing the limbus, and extending into the upper and lower conjunctival sacs where the eyelids and the curvature of the eye assist in retaining it in place. The device is paper-thin, on the order of 0.1 mm or less, so it is easy to position and comfortable for the patient. By sizing the device so that it does not intrude upon the sensitive limbus, the cornea is exposed and foreign-body awareness is reduced. Because the size of the eye does not vary significantly from person to person, the device may be manufactured in a single standard size (or a few sizes) to fit substantially all patients.

Another important feature of the present invention is its flexibility. The device is made of a highly flexible material so that, when placed on a patient's eye, it readily conforms to the shape of the eyeball. Unlike contact lenses and other devices that must be fitted individually for each patient, the invention does not need to be shaped to conform to the curvature of the eyeball. Therefore, its simplicity makes it easy to manufacture. If desired, a plurality of equally-spaced radial slits may be formed in the body of the device to increase its ability to flex and engage the eyeball.

Still another feature of the present invention is the material. The device is made of a porous, flexible, filter-paper-type material that maintains its structural integrity when wet, rather than a sponge-type material and has good wicking action. That is, the overall volume does not change appreciably when the device absorbs a liquid, since the liquid is absorbed into the pores rather than into the structure of the material itself. (In contrast, the volume of a sponge-type material may change noticeably upon absorption of water, sometimes by a factor of two or more.) The dimensional stability of the ocular medicator increases patient acceptance of the device, since the patient's reaction to it as a foreign-body is minimal. Suitable materials include non-irritating, non-allergenic filter-paper-type materials that are insoluble in lacrimal fluids, for example, methylcellulose and similar materials.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a front view of an ocular appliance according to a preferred embodiment of the present invention;

FIG. 2 is a cross-sectional view of the appliance of FIG. 1, taken along line 2—2 of FIG. 1;

FIG. 3 is a front view of a human eye, showing the appliance of FIG. 1 positioned for delivery of a liquid; and FIG. 4 is a cross-sectional view of the human eye of FIG. 3, taken along line 4—4 of FIG. 3, showing the appliance of FIG. 1 extending into the upper and lower conjunctival sacs.

DETAILED DESCRIPTION OF A PREFERRED EMBODIMENT

In the following description, like reference numerals refer to and identify the same structures, portions or surfaces throughout the different figures.

Referring now to FIGS. 1 and 2, there is shown a device 10 according to a preferred embodiment of the present invention. Device 10 is a substantially planar, annular body with an inner edge 12, a concentric outer edge 14, and a plurality of slits 16 extending from edge 14 into the body of the device. Device 10 has an inner diameter 18, an outer diameter 20, and an approximately uniform thickness 22.

Device 10 is placed on the eye to dispense a liquid to the cornea over a relatively brief period of time (on the order of minutes). FIGS. 3 and 4 show device 10 positioned in an eye 30 having an upper eyelid 32 and a lower eyelid 34. Eye 30 includes two generally spherical sections, a posterior section or sclera 36, commonly referred to as the white of the eye, and an anterior, transparent section or cornea 38. An iris 40 and a pupil 42 are visible through cornea 38.

Sclera 36 and cornea 38 are approximately spherical, with sclera 36 having a larger radius of curvature than cornea 38. The junction of cornea 36 and cornea 38 defines a limbus 44, also termed a corneal-scleral junction, at the point where the white sclera joins the transparent cornea. Cornea 38 contains a high concentration of nerve endings that serve to protect the cornea from dryness and injury from foreign objects. Limbus 44 defines the outer limit of the region in which an ocular insert designed for the delivery of medication should not intrude, otherwise, the natural, protective mechanisms (blinking, tearing) of the eye will be activated to expel the device from the eye.

As best seen in FIG. 4, eye 30 has an upper conjunctival sac 46 and a lower conjunctival sac 48, formed by a thin mucous membrane that connects the inner sides of eyelids 32, 34, respectively, to the eyeball. Conjunctival sacs 46, 48 surround the eyeball and prevent foreign objects from migrating under eyelids 32, 34 to areas within the orbit behind the eyeball. Conjunctival sacs 46, 48 also serve as a reservoir for lacrimal fluids which are wiped across the cornea by blinking the eyelids as needed to prevent corneal dryness and expel foreign bodies.

Device 10 is centered on pupil 42 and iris 40, circumscribing limbus 44 without intruding upon the limbus, and extending into upper and lower conjunctival sacs 46, 48. Inner diameter 18 of device 10 is slightly greater than the diameter of cornea 38, preferably at least approximately 1–2 mm greater so that inner edge 12 is centered on limbus 44 and spaced apart from the limbus. Outer diameter 20 is slightly smaller than an arcuate distance 50 between upper and lower conjunctival sacs 46, 48.

The dimensions of device 10 are determined by the size of the eye and the size of device that can be conveniently inserted into and removed from the eye. For use in humans, inner diameter 18 is preferably at least approximately 1–2 mm greater than the diameter of limbus 44 to prevent intrusion upon the limbus. Thus, inner diameter 18 is between 10–12 mm, preferably approximately 11 mm for the average size eye. To fit comfortably in conjunctival sacs 46, 48, outer diameter 20 is at least approximately 1–2 mm less than distance 50, that is, between 16 mm and 18 mm, preferably approximately 17 mm. The radial width of device 10, as measured from inner edge 12 to outer edge 14, is approximately 2–4 mm, preferably on the order of 3 mm.

Radial slits 16 (if present) are approximately one-half the width of device 10 in length, that is, for a width of 3 mm, slits 16 extend about 1.5 mm radially outwardly from inner edge 12. Device 10 preferably has at least three equally-spaced slits 16 to help the device conform to the shape of eye 30, more preferably, four or more slits. If desired, similar slits may be formed along the outer edge of device 10.

For patient comfort, device 10 must be as thin as possible consistent with ease of handling. Thickness 22 is less than approximately 0.5 mm, more preferably less than approximately 0.1 mm, and most preferably less than approximately 0.05 mm. The dimensions of the eye may vary somewhat from person to person, however, a device 10 with the above-described dimensions will be usable for almost all patients. If desired, the dimensions of device 10 may be adjusted for use with different groups of patients, for example, a smaller inner 18 and outer diameter 20 may be appropriate for infants, while larger inner and outer diameters may be useful for patients with larger-than-average eyes. For use in animals, device 10 can be dimensioned according to the size of the eye.

Device 10 is made of a flexible, porous, non-irritating, non-allergenic material that is insoluble in lacrimal fluids and does not disintegrate when wet. In addition, liquids are absorbed into the pores rather than into the structure of the material itself, thus, the volume of device 10 does not increase appreciably when the device is wet. Suitable materials include cellulosic materials, that is, cellulose and its derivatives (esters (cellulose acetate), ethers (methylcellulose), oxidized cellulose and regenerated cellulose (rayon)). Most preferably, device 10 is made of a filter paper material such as methylcellulose and similar materials.

In use, device 10 is placed in the eye generally as shown in FIGS. 3 and 4, and a quantity of a liquid medication is applied to the device using a squeeze tube, eye dropper or other suitable means. The liquid spreads rapidly through device 10, is diffused uniformly through the surface of the device, and carried over the eyeball by the lacrimal fluid and the blinking action of eyelids 32, 34. Device 10 is held in position by capillary forces and the curvature of sclera 36, thus, movement of the eyeball does not have a tendency to dislodge the device. If needed, additional quantities of the liquid are added 1–2 drops at a time to device 10.

Any liquids used to treat the eye, and intended to be delivered within a relatively short period of time (on the order of minutes), can be administered using device 10. Suitable liquid medications include topical anesthetic agents for ophthalmic surgery, antibiotics (tetracycline, chlortetracycline, bacitracin, neomycin, etc.), antibiotic and antiviral agents for treatment of infections, antiallergenics, decongestants, anti-inflammatories, miotics and anticholinesterases, mydriatics, sympathomimetics and so forth.

The amount of the selected liquid added to device 10 depends on the particular liquid, the therapeutic dosage, and so forth. Therefore, it is not feasible to attempt to define a range for the amount to be added to device 10; however, the dosage will be determinable by those skilled in the art of eye medication. Typically, approximately 1–2 drops at a time is used, however, additional amounts may be added from time to time as needed.

Device 10 may be used to deliver a liquid anesthetic such as proparacaine hydrochloride, tetracaine hydrochloride, or other fast-acting topical anesthetic. The liquid anesthetic is added to device 10, then the device is left in place on the eye for a sufficient period of time for the anesthetic to diffuse into the lacrimal fluids and anesthetize the sensitive corneal region. Typically, diffusion of the anesthetic requires at least 20 seconds and may take several minutes for some anesthetics. Then, device 10 is removed and the surgeon proceeds with the scheduled procedure. However, device 10 may be left in place and more anesthetic added at intervals to maintain anesthesia for the duration of the procedure. Thus, device 10 may be used to deliver topical anesthetics for procedures including intraocular surgery, suture removal, tonometry, gonioscopy, removal of foreign bodies, conjunctival and corneal epithelium scraping for diagnostic purposes, refractive surgery, and other corneal and conjunctival procedures of short duration. Since device 10 is dimensioned to peripherally surround limbus 44, edges 12, 14 and slits 16 can serve as a guide for positioning instruments for procedures such as refractive surgery where precise positioning is needed.

When device 10 is positioned in the eye, lacrimal fluids and the blinking action of eyelids 32, 34 carry liquids diffused through the surface of the device over the eyeball and allow the medication to operate in the eye and the surrounding regions. Substantially all of the liquid is delivered where needed; none collects in the corners of the eye or the conjunctival sacs where it can spill out or be expelled by blinking. Device 10 is held in position by capillary action, thus, movement of the eyeball does not tend to dislodge the device. Device 10 is sized to remain outside of the highly sensitive corneal region to prevent irritation and mitigate the foreign-body awareness problem.

Because of its thinness and flexibility, device 10 is easy to position on the eye and is readily tolerated by most patients. It is sufficiently flexible to conform to the shape of the individual patient's eyeball, and one or a few sizes will fit most all patients. The device is simple and economical to manufacture, since it is substantially planar and made in a single size (or a few standard sizes). Device 10 delivers liquid medication where it is needed accurately, quickly and without spillage; unlike eye droppers, wash glasses and the like, none enters the tear duct. In addition, the liquid is delivered more uniformly to the region surrounding limbus 44, a particular advantage of device 10 is used to deliver a local anesthetic agent for ophthalmic surgery.

It will be apparent to those skilled in the art that many changes and substitutions can be made to the preferred embodiment herein described without departing from the spirit and scope of the present invention as defined by the appended claims.

What is claimed is:

1. A device for delivering a liquid to an eye, said eye having a limbus with a diameter, an upper conjunctival sac and a lower conjunctival sac, said upper and lower conjunctival sacs being separated by an arcuate distance, said device comprising a flexible, substantially planar, annular body having an inner edge and an outer edge, said inner edge having a diameter greater than said diameter of said limbus, said outer edge having a diameter less than said arcuate distance, said body being made of solid cellulosic material, said body having a plurality of radial slits extending radially outwardly from said inner edge.

2. The device as recited in claim 1, wherein said inner diameter is at least approximately 1 mm greater than said diameter of said limbus.

3. The device as recited in claim 1, wherein said outer diameter is at least approximately 1 mm less than said arcuate distance.

4. The device as recited in claim 1, wherein said inner diameter is at least approximately 1 mm greater than said diameter of said limbus and said outer diameter is at least approximately 1 mm less than said arcuate distance.

5. The device as recited in claim 1, wherein said body is less than approximately 0.1 mm thick.

6. The device as recited in claim 1, wherein said solid cellulosic material is methylcellulose.

7. A device for delivering an anesthetic to an eye, said eye having a limbus with a diameter, an upper conjunctival sac and a lower conjunctival sac, said upper and lower conjunctival sacs being separated by an arcuate distance, said device comprising a porous, substantially planar, annular body having edges defined by an inner ring and an outer ring, said inner ring having a diameter greater than said diameter of said limbus, said outer ring having a diameter less than said arcuate distance, said body being made of solid cellulosic material, said body further including conforming means for enabling said body to conform to the shape of said eye, said conforming means comprising a plurality of radial slits formed in said body extending outwardly from said inner ring.

8. The device as recited in claim 7, wherein said inner diameter is at least approximately 1 mm greater than said diameter of said limbus, and wherein said outer diameter is at least approximately 1 mm less than said arcuate distance.

9. The device as recited in claim 7, wherein said inner diameter is approximately 11 mm, and wherein said outer diameter is approximately 17 mm.

10. The device as recited in claim 7, wherein said body is no more than approximately 0.05 mm thick.

11. The device as recited in claim 7, wherein said body is made of a flexible, non-allergenic material that is dimensionally and structurally stable when wet.

12. The device as recited in claim 7, wherein said said solid cellulosic material is methylcellulose.

13. A device for delivering liquid to an eye, said eye having a limbus with a diameter, an upper conjunctival sac and a lower conjunctival sac, said upper and lower conjunctival sacs being separated by an arcuate distance, said device comprising:

a porous, substantially planar, annular body having edges defined by an inner ring and an outer ring, said inner ring having a diameter greater than said diameter of said limbus, said outer ring having a diameter less than said arcuate distance, said body having a plurality of slits formed therein, each slit extending radially outwardly from said inner ring for enabling said body to conform to the shape of said eye when said body is positioned about said limbus.

14. The device of claim 7, further comprising liquid carried by said body.

15. The device of claim 13, wherein said body is made of solid cellulosic material.

16. A device for delivering a liquid to an eye, said eye having a limbus with a diameter, an upper conjunctival sac and a lower conjunctival sac, said upper and lower conjunctival sacs being separated by an arcuate distance, said device comprising a flexible, substantially planar, annular body having an inner edge and an outer edge, said inner edge having a diameter greater than said diameter of said limbus, said outer edge having a diameter less than said arcuate distance, said body having a plurality of tapered slits formed therein, each of said slits having a first end opening toward an edge of said body and a second end terminating at a point within said body.

17. The device of claim 16, wherein said body is made of solid cellulosic material.

* * * * *